(12) United States Patent
Rawlinson et al.

(10) Patent No.: US 11,357,573 B2
(45) Date of Patent: Jun. 14, 2022

(54) OPTIMUM TREATMENT PLANNING DURING CORONARY INTERVENTION BY SIMULTANEOUS SIMULATION OF A CONTINUUM OF OUTCOMES

(71) Applicant: INTERNATIONAL BUSINESS MACHINES CORPORATION, Armonk, NY (US)

(72) Inventors: Andrew Rawlinson, Kensington (AU); Kerry Halupka, Northcote (AU); Stephen Michael Moore, Melbourne (AU); Sergiy Zhuk, Dublin (IE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 323 days.

(21) Appl. No.: 16/394,092

(22) Filed: Apr. 25, 2019

(65) Prior Publication Data
US 2020/0337773 A1 Oct. 29, 2020

(51) Int. Cl.
*G16H 50/00* (2018.01)
*G06T 7/13* (2017.01)
(Continued)

(52) U.S. Cl.
CPC .............. *A61B 34/10* (2016.02); *A61B 5/026* (2013.01); *A61B 5/02007* (2013.01);
(Continued)

(58) Field of Classification Search
CPC .......... G16H 30/40; G16H 50/00; G06T 7/55; G06T 7/194
See application file for complete search history.

(56) References Cited

U.S. PATENT DOCUMENTS 8,157,742 B2 4/2012 Taylor
9,042,613 B2 5/2015 Spilker et al.
(Continued)

OTHER PUBLICATIONS

Chiastra, C., "Patient-Specific Modeling of Stented Coronary Arteries Reconstructed from Optical Coherence Tomography: Towards a Widespread Clinical Use of Fluid Dynamics Analyses" J. of Cardiovasc. Trans. Res. (2018) 11:156.

(Continued)

*Primary Examiner* — Michael Tomaszewski
*Assistant Examiner* — Jay M. Patel
(74) *Attorney, Agent, or Firm* — Cantor Colburn LLP; Joseph Petrokaitis (57) ABSTRACT

A technique relates to coronary reconstruction. Angiogram data associated with cardiac catheterization of an artery for a subject is received, where a contrasting agent is used during the cardiac catheterization. Frames that match from the angiogram data are selected, the frames being from different views. Two-dimensional ordered point clouds for the frames are formed. A three-dimensional ordered point cloud of a reconstructed coronary artery for the subject from the two-dimensional ordered point clouds of the frames is formed. Observed contrast motion caused by the contrasting agent onto the reconstructed coronary artery is mapped, the reconstructed coronary artery thereby providing a three-dimensional model of the artery of the subject during the cardiac catheterization.

19 Claims, 7 Drawing Sheets

(51) Int. Cl.
  *G06T 7/194* (2017.01)
  *G06T 7/55* (2017.01)
  *G16H 30/40* (2018.01)
  *A61B 34/10* (2016.01)
  *A61B 5/026* (2006.01)
  *A61B 5/02* (2006.01)
  *A61B 6/00* (2006.01)

(52) U.S. Cl.
  CPC .............. *A61B 6/481* (2013.01); *A61B 6/504* (2013.01); *G06T 7/13* (2017.01); *G06T 7/194* (2017.01); *G06T 7/55* (2017.01); *G16H 50/00* (2018.01); *A61B 2034/101* (2016.02); *A61B 2034/107* (2016.02); *G06T 2207/20044* (2013.01); *G06T 2207/30048* (2013.01); *G06T 2207/30172* (2013.01); *G16H 30/40* (2018.01)

(56) References Cited

U.S. PATENT DOCUMENTS

| | | | |
|---|---|---|---|
| 9,043,191 B2 | 5/2015 | Grady et al. | |
| 2012/0203530 A1 | 8/2012 | Sharma et al. | |
| 2012/0282583 A1* | 11/2012 | Thaler | G09B 23/30 434/267 |
| 2013/0132054 A1 | 5/2013 | Sharma et al. | |
| 2014/0088990 A1* | 3/2014 | Nawana | G16H 50/20 705/2 |
| 2014/0204190 A1* | 7/2014 | Rosenblatt, III | G16H 70/20 705/2 |
| 2015/0131886 A1* | 5/2015 | Aben | G06T 7/32 382/132 |
| 2015/0223746 A1* | 8/2015 | Bonnet | G16H 40/63 600/301 |
| 2015/0317793 A1* | 11/2015 | Zhang | G06T 5/50 382/130 |
| 2015/0339051 A1* | 11/2015 | Yang | G06F 3/167 382/189 |
| 2015/0347682 A1* | 12/2015 | Chen | G16H 80/00 705/2 |
| 2016/0148372 A1* | 5/2016 | Itu | A61B 8/5223 382/128 |
| 2017/0330487 A1* | 11/2017 | Harlev | G06F 3/04845 |
| 2018/0153495 A1* | 6/2018 | Itu | A61B 6/032 |
| 2018/0174490 A1* | 6/2018 | Randles | G09B 23/303 |
| 2018/0289252 A1 | 10/2018 | Garnavi et al. | |
| 2018/0310830 A1* | 11/2018 | Baldauf | A61B 5/0084 |
| 2019/0318476 A1* | 10/2019 | Isgum | A61B 6/504 |
| 2020/0222018 A1* | 7/2020 | van Walsum | A61B 6/464 |

OTHER PUBLICATIONS

Duanmu, Z., "A patient-specific lumped-parameter model of coronary ciiculation," Scientific Reports, vol. 8, Article No. 874 (2018).

Quatember, B., "Patient-specific modelling and simulation of coronary haemodynamics." In Proceedings of the 2008 Spring simulation multiconference (SpringSim '08). Society for Computer Simulation International, San Diego, CA, USA, 573-580, 2008.

Zifan, A.,"Patient-Specific Computational Models of Coronary Arteries Using Monoplane X-Ray Angiograms," Computational and Mathematical Methods in Medicine, vol. 2016, Article ID 2695962, 12 pages, 2016.

Halupka, K., et al., "Deep Semantic Instance Segmentation of Tree-like Structures Using Synthetic Data," Grace Period Disclosure, arXiv:1811.03208v1 [cs.CV], Nov. 8, 2018, 10 pages.

\* cited by examiner

OPTIMUM TREATMENT PLANNING DURING CORONARY INTERVENTION BY SIMULTANEOUS SIMULATION OF A CONTINUUM OF OUTCOMES

BACKGROUND

The present invention generally relates to computing systems, and more specifically, to computer systems, computer-implemented methods, and computer program products configured to provide optimum treatment planning during coronary intervention by using simultaneous simulation of a continuum of outcomes.

STATEMENT REGARDING PRIOR DISCLOSURES BY THE INVENTOR OR A JOINT INVENTOR

The following disclosure is submitted under 35 U.S.C. 102(b)(1)(A): "Deep Semantic Instance Segmentation Of Tree-like Structures Using Synthetic Data", by Kerry Halupka, Rahil Garnavi, and Stephen Moore, Nov. 8, 2018, pages 1-10, the contents of which are incorporated herein by reference.

Cardiac catheterization (heart cath or simply cath) is the insertion of a catheter into a chamber or vessel of the heart for diagnostic and interventional purposes. A common example of cardiac catheterization is coronary catheterization that involves catheterization of the coronary arteries for coronary artery disease and myocardial infarctions ("heart attacks"). Catheterization is most often performed in special laboratories with fluoroscopy and highly maneuverable tables. These "cath labs" are often equipped with cabinets of catheters, stents, balloons, etc., of various sizes to increase efficiency. Monitors show the fluoroscopy imaging, electrocardiogram (EKG or ECG), pressure waves, and more. Access to the heart is obtained through a peripheral artery such as the radial or femoral artery. Once access is obtained, plastic catheters (tiny hollow tubes) and flexible wires are used to navigate to and around the coronary arteries.

Coronary angiography is a diagnostic procedure that allows visualization of the coronary vessels. Fluoroscopy is used to visualize the lumens of the arteries as a two-dimensional (2D) projection. Should these arteries show narrowing or blockage, then techniques exist to open these arteries, i.e., to increase blood flow to previously blocked (or occluded) vessels.

SUMMARY

Embodiments of the invention are directed to a computer-implemented method for coronary reconstruction. A non-limiting example of the method includes receiving, by a computer system, angiogram data associated with cardiac catheterization of an artery for a subject, wherein a contrasting agent is used during the cardiac catheterization, and selecting, by the computer system, frames that match from the angiogram data, the frames being from different views. Also, the method includes forming two-dimensional ordered point clouds for the frames, forming a three-dimensional ordered point cloud of a reconstructed coronary artery for the subject from the two-dimensional ordered point clouds of the frames, and mapping observed contrast motion caused by the contrasting agent onto the reconstructed coronary artery, the reconstructed coronary artery thereby providing a three-dimensional model of the artery of the subject during the cardiac catheterization.

Embodiments of the invention are directed to a computer system for coronary reconstruction. A non-limiting example of the computer system includes a processor, and memory communicatively coupled to the processor and comprising computer-executable instructions that, when executed by the processor, cause the processor to perform a method. A non-limiting example of the method includes receiving, by the processor, angiogram data associated with cardiac catheterization of an artery for a subject, wherein a contrasting agent is used during the cardiac catheterization, and selecting, by the processor, frames that match from the angiogram data, the frames being from different views. Also, the method includes forming two-dimensional ordered point clouds for the frames, forming a three-dimensional ordered point cloud of a reconstructed coronary artery for the subject from the two-dimensional ordered point clouds of the frames, and mapping observed contrast motion caused by the contrasting agent onto the reconstructed coronary artery, the reconstructed coronary artery thereby providing a three-dimensional model of the artery of the subject during the cardiac catheterization.

Embodiments of the invention are directed to a computer program product for coronary reconstruction, the computer program product comprising a computer readable storage medium having program instructions embodied therewith, wherein the computer readable storage medium is not a transitory signal per se, the program instructions executable by a computer system to cause the computer system to perform a method. A non-limiting example of the method includes receiving, by the computer system, angiogram data associated with cardiac catheterization of an artery for a subject, wherein a contrasting agent is used during the cardiac catheterization, and selecting, by the computer system, frames that match from the angiogram data, the frames being from different views. Also, the method includes forming two-dimensional ordered point clouds for the frames, forming a three-dimensional ordered point cloud of a reconstructed coronary artery for the subject from the two-dimensional ordered point clouds of the frames, and mapping observed contrast motion caused by the contrasting agent onto the reconstructed coronary artery, the reconstructed coronary artery thereby providing a three-dimensional model of the artery of the subject during the cardiac catheterization.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the embodiments of the invention, the various elements illustrated in the figures are provided with two or three digit reference numbers. With minor exceptions, the leftmost digit(s) of each reference number correspond to the figure in which its element is first illustrated.

DETAILED DESCRIPTION

Various embodiments of the present invention are described herein with reference to the related drawings. Alternative embodiments can be devised without departing from the scope of this invention. Although various connections and positional relationships (e.g., over, below, adjacent, etc.) are set forth between elements in the following description and in the drawings, persons skilled in the art will recognize that many of the positional relationships described herein are orientation-independent when the described functionality is maintained even though the orientation is changed. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. As an example of an indirect positional relationship, references in the present description to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

Turning now to an overview of technologies that are more specifically relevant to aspects of the invention, apart from preventive measures, early diagnosis and an efficient and appropriate treatment planning are key factors for addressing diseases of the cardiovascular system (CAD) like myocardial infarction and heart failure. The current gold standard for CAD diagnosis and treatment planning is coronary angiography. Coronary angiography is a minimally invasive procedure during which a catheter is guided towards the coronary arteries which are consequently flushed with a radio-opaque dye and dynamically imaged using an x-ray source (commonly C-arm). The doctor uses this catheter to put a contrast dye into the blood of the coronary arteries. The dye shows up on x-rays and highlights the coronary arteries. The x-rays are called angiograms. The procedure is usually repeated from different angles for a 3D assessment of the vascular structure. The sequence of images is interpreted visually by a cardiologist and assessed for presence, extent and severity of stenoses. C-arm is a medical imaging device that is based on x-ray technology and can be used flexibly within a clinic. The name is derived from the C-shaped arm used to connect the x-ray source and x-ray detector to one another. The x-ray source is a generator, and the x-ray detector can include an image intensifier of flat panel detector. The C-arm is often used in cardiology for intraoperative imaging. The device provides high-resolution x-ray images in real-time, allowing the surgeon to monitor progress at any point during the surgery.

However, coronary angiograms only provide limited detail on actual cardiac function, leaving the diagnosis and treatment plan a challenging process with potential for subjective and inaccurate decisions, and consequently, inappropriate treatment actions. Patients with multiple narrowing of cardiac vessels are at particular risk of sub-optimal treatment, as the differentiation between harmful, flow limiting stenoses and innocuous narrowing is challenging and unreliable. Stenosis is the abnormal narrowing of a passage in the arteries. Accurate treatment decisions are important not only for the individual patient's prognosis, but also for overall healthcare cost and efficient resource management, since sub-optimal treatments can lead to further complications, such as restenosis. The use of functional measures in addition to coronary angiograms has been shown through clinical testing to improve diagnosis and treatment planning. One such functional measure is fractional flow reserve (FFR), which is the ratio of distal coronary pressure to aortic pressure. Standard FFR acquisitions involve specialized catheter which are equipped with a pressure transducer to record blood pressure upstream and downstream of the vessel narrowing. The ratio of pressure readings around the stenoses are indicative of hemodynamic significance of the narrowing. Although shown to improve patient outcomes, the additional cost, time, training requirements, and potential difficulties during the FFR procedure have resulted in a relatively low acceptance of the technique into clinical practice.

Figure 1:
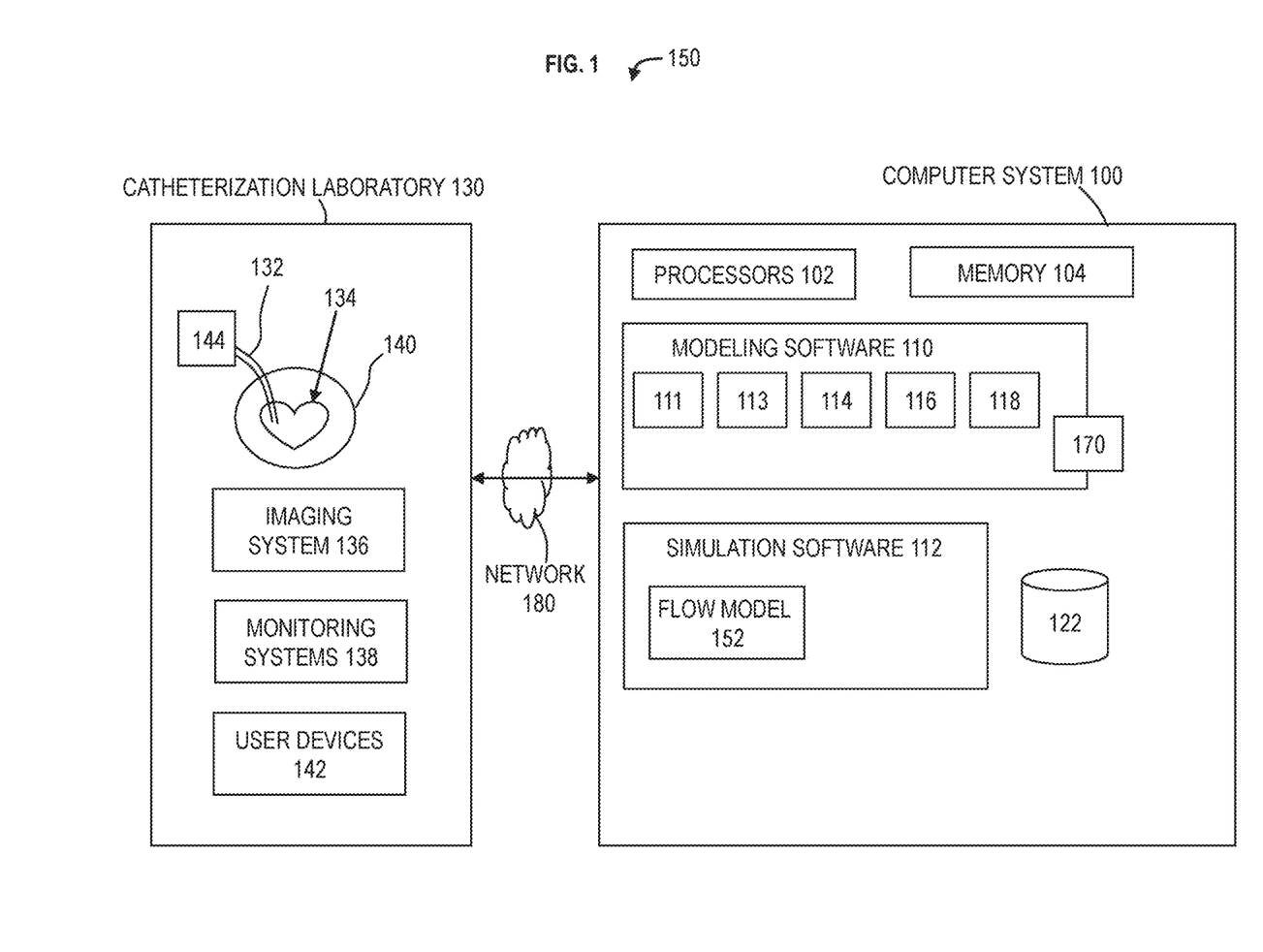
FIG. 1 depicts a system which includes one or more computer systems operatively connected to a catheterization laboratory according to embodiments of the invention.

Turning now to an overview of the aspects of the invention, one or more embodiments can estimate FFR through the use of computational fluid dynamics (CFD) applied to a patient specific geometrical model (without requiring standard FFR acquisitions utilizing the specialized catheter equipped with the pressure transducer to record blood pressure upstream and downstream of the vessel narrowing). This method, which can be referred to as virtual fractional flow reserve (vFFR), (as depicted in FIG. 1) reduces the cost of the procedure and has no need for specially trained operators. The real-time calculation of FFR parameters based on high-performance computing system/architecture enables an immediate treatment decision according to embodiments of the invention. For example, the treatment option can be if a stent placement is advisable this could be performed during the procedure superseding the need for a subsequent procedure. However, the difficulty of treatment planning during coronary angiography extends beyond whether or not to place a stent. The clinician must also consider the size and shape of stent, the number of stents (if multiple stenoses are present, which requires evaluating which stenoses are most contributing to the patient's difficulties), and/or whether a coronary arterial bypass graft (CABG) might be better suited. Embodiments of the invention are configured to simulate all possible treatment decisions in parallel, using real-time vFFR (which could be on-site or remote) with appropriately modified patient-specific coronary artery geometries. The outcomes of the simulations are then assessed using an objective function that is designed to either maximize blood flow or minimize pressure drop across a stenosis. Additionally, terms in the objective function will encourage a reduced number of stents and/or bypass grafts, reduced FFR values in larger vessels and increased shear stress in larger vessels (to reduce the possibility on future stenoses). The embodiments of the invention allow for the clinician to manually alter the relative importance of elements of the objective function.

The simulations are run on the computer system (which could be on-site or remote) in real-time and the optimal treatment plan, based on the minimization of the objective function, is then reported to the clinician. Thus, the clinician can be informed of and take the optimal course of action during a single catheter laboratory visit (i.e., while the heart catheterization is occurring). This serves to save clinician time, reduce resource waste, optimize patient outcomes, and reduce the cost of interventions.

Although the state-of-the-art may aim to simulate multiple interventional outcomes, the state-of-the-art requires the use of computerized tomography (CT) scanning of the heart and is therefore used at an earlier stage of the treatment pipeline (i.e., prior to heart catheterization). A computerized tomography (CT) scan combines a series of x-ray images taken from different angles around your body and uses computer processing to create cross-sectional images (slices) of the bones, blood vessels, and soft tissues inside your body. Additionally, using only CT requires assumptions to be made about the velocity of blood flow through the arteries. This information is vital to the accurate estimation of vFFR, and errors here can therefore drastically impact the outcome. The simulation using the CT scan does not account for the data obtained during the heart catheterization. Further, embodiments of the invention are configured to automatically simulate, and rate multiple outcomes based on the heart catheterization data while the patient is undergoing the procedure.

Embodiments of the invention describe a computer system capable of building patient specific computer simulations of coronary blood hemodynamics to provide quantitative predictions. The computer system considers the immediate and long-term success of a variety of treatments and thereby provides advice to the clinician on the most appropriate course of action. The computer system specifically targets Invasive Coronary Angiography as the procedure used to obtain the anatomical and functional information needed to reconstruct and tune the patient specific models. In some implementations, the computer system can leverage analytics executing on state-of-the-art IBM® PowerAI systems in order to perform the predictive simulations within the time frame of these procedures (simultaneous with the cardiac catheterization, i.e., heart catheterization), when decisions on how to intervene need to be made. Unlike the state-of-the-art, embodiments of the invention directly apply to coronary angiography, where the velocity of blood flow can be estimated for each individual patient (depicted in FIG. 1), thereby improving the accuracy of simulations.

Turning now to a more detailed description of aspects of the present invention, FIG. 1 depicts a system 150 which includes one or more computer systems 100 operatively connected to a catheterization laboratory 130 according to embodiments of the invention. The computer system 100 can be in the catheterization laboratory 130 and/or remote from the catheterization laboratory 130. The catheterization laboratory 130 includes a standard catheter laboratory control room with all standard equipment and systems as understood by one skilled in the art. The catheterization laboratory 130 includes a patient 140 in which a catheter 132 is guided into the coronary arteries of the heart 134 of the patient 140. The coronary arteries are flushed with a contrast agent (i.e., dye) and dynamically imaged using an imaging system 136 (e.g., C-arm having one or more x-ray sources correspondingly matched with one or more x-ray detectors). The dye appears on x-rays, e.g., x-ray angiograms, and highlights the coronary arteries. The doctor can view the x-ray angiograms on user devices 142 which can include display devices, touch screens, joysticks, keyboards, etc. The user devices 142 can include computers, such as laptops, desktops, workstations, tables, etc.

The coronary arteries are the arteries of the coronary circulation, which transport blood into the cardiac muscle. They are mainly composed of the left and right coronary arteries, both of which give off branches. The left coronary artery arises from the aorta above the left cusp of the aortic valve and feeds blood to the left side of the heart. The right coronary artery originates from above the right cusp of the aortic valve, and it travels down the right coronary sulcus, towards the crux of the heart.

Monitoring systems 138 can include and be representative of various devices including an electrocardiogram (ECG, also referred to as EKG). The electrocardiogram is a heart test that tracks the electrical activity (referred to as an ECG/EKG trace) of the heart and records it on a moving paper and/or displays it as a moving line on a screen. The monitoring systems 138 can include a device for obtaining the patient's systemic blood pressure. Systemic blood pressure refers to the pressure exerted on blood vessels in systemic circulation and is often measured using arterial pressure, or pressure exerted upon arteries during heart contractions. Arterial blood pressure is the pressure of the blood within an arterial vessel, typically the brachial artery in the upper arm. The systemic blood pressure can be approximately determined from measurements of the systolic pressure and the diastolic pressure while there is a normal resting heart rate.

The monitoring systems 138 can collect contrast injection information for the dye injected in the heart 134 via the catheter 132 and dye injection device 144. The dye injection device 144 can include a pump mechanism that injects the dye at specific times. The monitoring system 138 can include intravascular imaging modalities such as Intravascular Ultrasound (IVUS), or Optical Coherence Tomography (OCT), which capture intravascular images.

The data from the imaging system 136 and the monitoring systems 138 (catheterization laboratory 130) is transferred to the computer system 100 via a network 180 (wired and/or wireless) in real-time (while the patent is undergoing the heart catheterization). The computer system 100 is configured to take as input multiple coronary x-ray angiograms combined with a patient's systemic blood pressure, ECG trace, contrast injection information, and/or intravascular imaging. The data from the imaging system 136 and the monitoring systems 138 can be collected by the user devices 142 and transferred to the computer system 100. Also, the computer system 100 can request the data from the imaging system 136 and the monitoring systems 138 and/or the data can be pushed to the computer system 100.

The computer system 100 includes processors 102, memory 104, modeling software 110, and simulation software 112. The modeling software 110 is configured to generate a reconstructed coronary artery which is a 3D model 170 of the patient's coronary artery in the heart 134 presently undergoing heart catheterization. The computer system 100 is configured to generate a 3D model 170 of the left coronary artery and the right coronary artery according to the data transferred from the imaging system 136 and the monitoring systems 138. The simulation software 112 is configured to use the 3D model 170 of reconstructed coronary artery and a flow model 152 to simulate blood flow through the 3D model 170.

Figure 2:
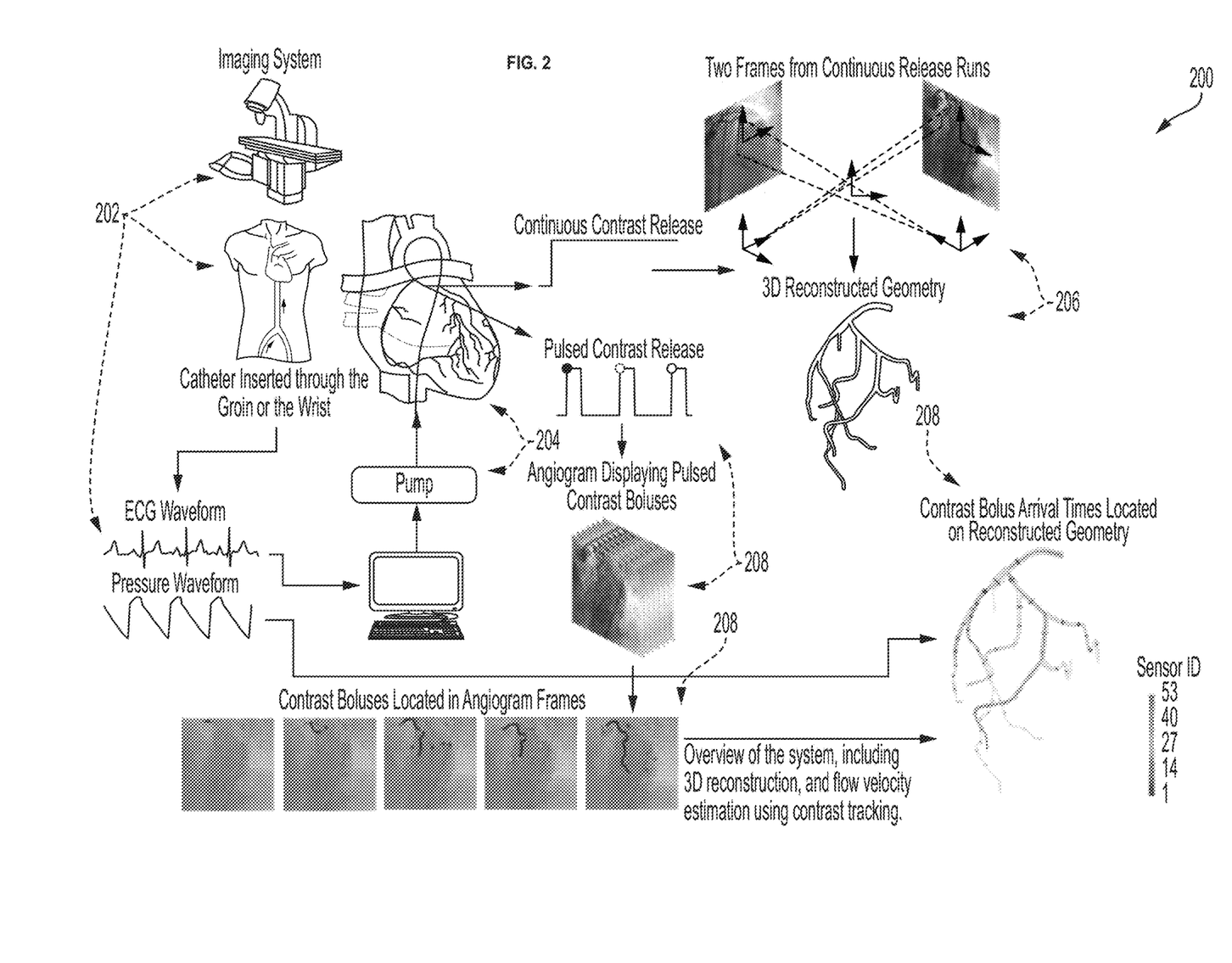
FIG. 2 depicts a high-level system overview of the system during the coronary catheterization according to embodiments of the invention.

FIG. 2 depicts a flow 200 as high-level system overview of the system 150 during the coronary catheterization of the patient 140 according to embodiments of the invention. FIG. 2 illustrates 3D reconstruction and flow velocity estimation using contrast tracking of dye flowing in the artery. At block 202, the catheter 132 is inserted into the patient's heart 134 for imaging by the imaging system 136 while the systemic pressure and the ECG waveform are monitored by the monitoring system 138.

At block 204, the contrast injection device 144 is controlled (e.g., via a user device 142) to pump the contrast agent into the artery of the patient while the imaging system 136 takes x-rays of the artery (which includes the various branches) as angiograms. The monitoring system 138 receives and stores the dye contrast information (e.g., timing of injections) from the dye injecting device 144.

At block 206, the computer system 100 is continuously receiving x-ray angiograms (i.e., x-ray video) of the artery in the heart 134 which shows the contrast agent flowing through the artery along with the monitoring data from monitoring system 138. The imaging system 136 can be monoplane scanner/system or a biplane scanner/system. A monoplane system acquires one video, rotates and acquires another video (from a different view), and so forth. A biplane system has two x-ray scanners and two x-ray detectors, such that they can both record two videos simultaneously (from different views) before rotating to a different view. Assuming a monoplane system which is more prevalent, the modeling software 110 of the computer system 100 is configured to select two still frames from the two videos which are from different views. The modeling software 110 finds and selects the two still frames from the same cycle of the heart using the ECG trace, such as when the heart contracts which is at the spike of the ECG trace. The modeling software 110 is configured to use the two frames to find a matching point and then project/reconstruct the 3D geometry of the artery as the 3D reconstructed artery 170 (i.e., 3D model). The modeling software 110 has to check and ensure that the two frames have a matching point in order to perform the 3D projection. Further detail of the 3D reconstruction is discussed in FIG. 3. When a biplane system/scanner is used to acquire the two videos, modeling software 110 is not required to find and select two still frames with a matching point at the same cycle (contraction or relaxed) because the two frames are taken simultaneously. There will be a matching point from different views automatically provided in the video using the biplane system/scanner, and the modeling software 110 can select two still videos having the same timestamp.

At block 208, the simulation software 112 uses the 3D model 170 and the flow model 152 to perform simulations. The flow model 152 of the simulation software 112 represents and uses pulsed contrast release data which is part of the contrast injection information of the injected dye, angiograms displaying pulsed contrast boluses, and the pressure waveform of the systemic pressure to recreate and simulate the blood flow through the 3D model 170. Particularly, the flow model 152 represents the timing and location of the contrast (i.e., dye) in the artery to recreate the timing of blood flow for the simulation. Bolus tracking is a technique used in computed tomography imaging to optimize timing of the imaging and can be utilized in flow model 152. A small bolus of radio-opaque contrast media (i.e., dye) is injected into a patient via the catheter 132. Depending on the vessel being imaged, the volume of contrast is tracked using a region of interest (abbreviated "R.O.I.") by the flow model 152. Images (i.e., x-ray video) are acquired at a rate as fast as the contrast moving through the blood vessels. A flow velocity estimation is made using the contrast tracking in the flow model 152.

Figure 3:
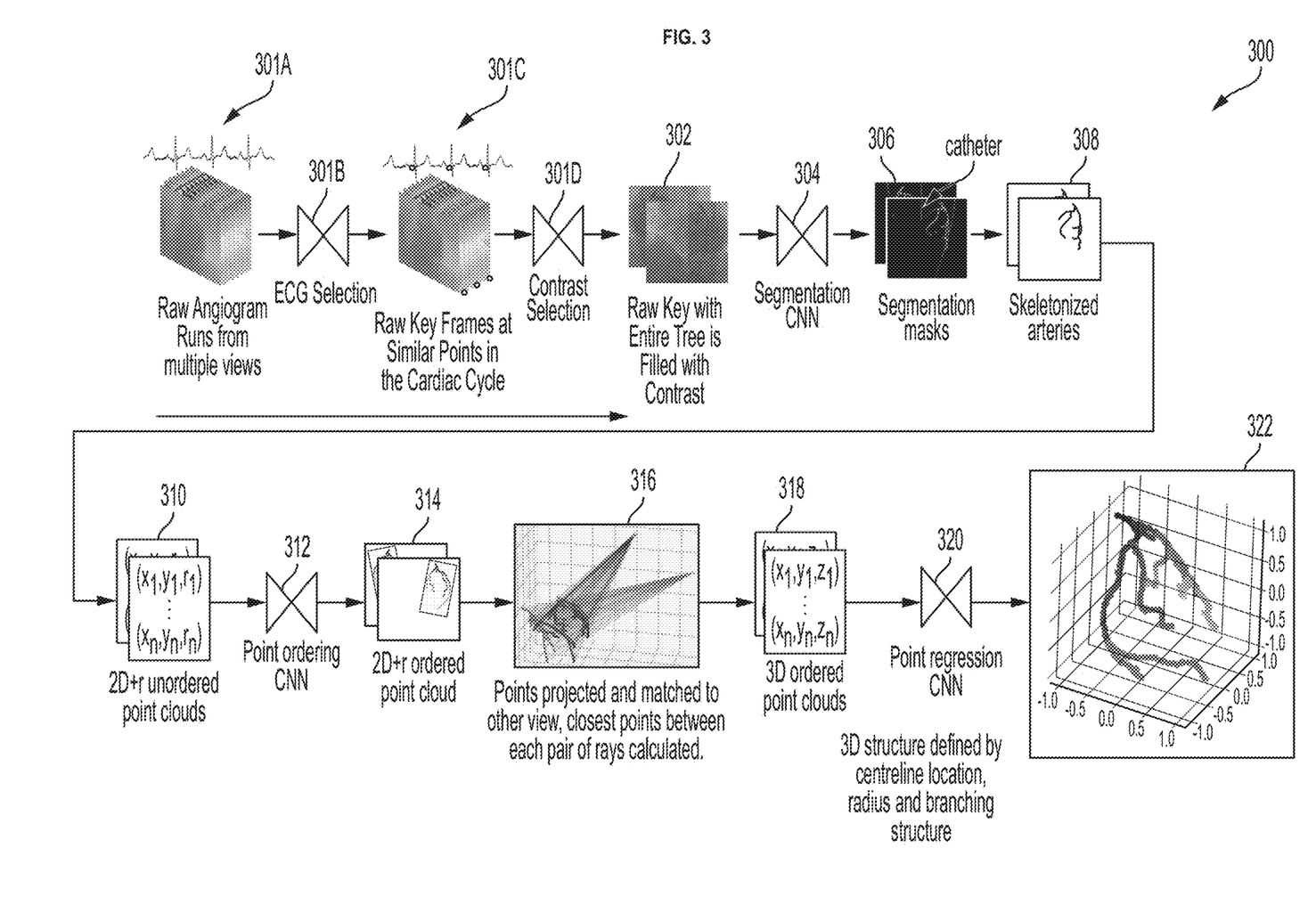
FIG. 3 depicts a pipeline for automatic reconstruction of a patient specific three-dimensional model during the coronary catheterization according to embodiments of the invention.

FIG. 3 depicts an example pipeline flow 300 of the 3D reconstruction of reconstructed artery 170 (i.e., 3D model) during the coronary catheterization of the patient 140 according to embodiments of the invention. FIG. 3 continues from blocks 202, 204, and 206 discussed in FIG. 2. The image processing pipeline begins with a pair of angiograms (runs), each of which is comprised of a set of image frames animating the cardiac and dye motion and includes as metadata the patient's ECG trace along with the C-Arm imaging parameters. For example, at blocks 301A and 301B, the modeling software 110 of the computer system 100 receives the angiograms and ECG traces which are input to an ECG selection CNN that has been trained to locate key phases in the ECG trace (e.g. the QRS complex which refers to the combination of three of the graphical deflections seen on a EKG or ECG) and outputs numbered keyframes from the two runs at block 301C. At block 301D, the keyframes are input into a contrast selection CNN that has been trained to identify those frames where the radio-opaque contrast agent has traversed the whole way through the coronary tree. One keyframe from each run that presents the entire vascular tree at a corresponding point in the cardiac cycle is then selected. These two selected frames are then passed into a semantic segmentation CNN, that has been trained on manually annotated data angiogram frames to apply separate classifications to the arterial lumen, the catheter, and the remaining background, as discussed further below at block 302 and 304. The modeling software 110 can use various techniques for selection, segmenting, ordering, etc., including thresholding methods, clustering methods (such the K-means algorithm which is an interactive technique), motion and interactive segmentation, histogram-based methods, etc. Additionally, in some implementations, the modeling software 110 can use machine learning techniques such as an ECG selection convolutional neural network (CNN) 111, a contrast selection CNN 113, and a semantic segmentation CNN 114 depicted in FIG. 1. CNN is also referred to as deep learning. Deep learning is a specific method of machine learning that incorporates neural networks in successive layers to learn from data in an iterative manner. A CNN is a specific type of neural network architecture that can be used for image processing-based tasks and functions by aggregating (or performing 'convolutions') between input pixels and neural weights and biases, as image data is fed through the network. Deep learning is especially useful when learning patterns from unstructured data. Neural networks and deep learning are often used in image recognition, speech, and computer vision applications.

Continuing block 302, from the two videos acquired by the monoplane system/scanner using the same spatial condition of the ECG trace (both at the point of a spike) and/or from the two videos acquired by biplane system/scanner, the modeling software 110 of the computer system 100 selects a still frame from one video and another still frame from the other video. The two still frames of the artery are from different views. It is noted that the before selecting the still frames, the modeling software 110 of the computer system 100 is configured to separate the angiogram (videos) into frames where the contrast agent is moving through the entire tree (i.e., the arterial segments) and removes the frames where the contrast agent has been flushed out. For the frames (of both videos) where the contrast agent is moving through the entire tree (i.e., the arterial segments), the modeling software 110 is configured to use these frames to select the two frames. The term tree reflects that the artery includes branches that connect to a trunk or main part as understood by one skilled in the art.

At block 304, the modeling software 110 of the computer system 100 is configured to perform image segmentation for the selected still frames, which results in segmentation masks of the two frames at block 306. Image segmentation is the process of partitioning a digital image into multiple segments (sets of pixels, also known as super-pixels). Image segmentation is used to locate objects and boundaries (lines, curves, etc.) in images. More precisely, image segmentation is the process of assigning a label to every pixel in an image such that pixels with the same label share certain characteristics. Accordingly, the modeling software 110 of the computer system 100 is configured to perform classification of the pixels in each of the selected still frames using, for example, the segmentation CNN 114. The modeling software 110 classifies the pixels as background, arterial structure (i.e., artery), catheter, etc.

The modeling software 110 removes (i.e., subtracts) the identified background pixels and the catheter pixels from the two frames of the segmentation masks, and then perform skeletonization of the artery which results in the skeletonized arteries at block 308. Skeletonization is a process for reducing foreground regions in a binary image to a skeletal remnant that preserves the extent and connectivity of the original region while removing most of the original foreground pixels. Particularly, the skeleton (or topological skeleton) of a shape is a thin version of that shape that is equidistant to its boundaries. The skeleton emphasizes geometrical and topological properties of the shape, such as its connectivity, topology, length, direction, and width. Together with the distance of its points to the shape boundary, the skeleton can also serve as a representation of the shape (they contain all the information necessary to reconstruct the shape). Accordingly, using the skeletonized arteries for the frames, the modeling software 110 generates unordered point clouds which are 2D+r unordered point clouds for the two images at block 310. A point cloud is a set of data points in space. The 2D+r unordered point clouds have coordinates for each point representing the artery respectively in both frames along with the radius associated at each point. To build the point cloud for each respective frame, the modeling software 110 is configured to scan the skeletonized artery in the frame and obtain an x, y, r component for each point, where x is the value (i.e., location) along the x-axis, y is the value along the y-axis, and r is the radius because the artery has a round/spherical shape. This is performed for each of the frames which results in a collection of points (x, y, r) with each data point having its respective radius. The radius r is obtained from finding the centerline of each point along the line representing the artery of block 308, and the radius is the thickness of the line.

At block 312, modeling software 110 is configured to group the 2D+r unordered point clouds to 2D+r ordered point clouds of block 314. The modeling software 110 is configured to group points into arterial segments (arterial points, e.g., of the trunk) and identify branch segments (branch points which extend from the trunk and/or other branches). The modeling software 110 orders the locations of the point, e.g., by assigning a color or label moving along the tree. Because some parts of the artery can branch (and/or overlap), the modeling software 110 identifies the correct branches. In some implementations, this point ordering can be performed using point ordering CNN 116 depicted in FIG. 1. The point ordering CNN 116 takes as input two sets of unordered point clouds, where each point cloud corresponds to the points along the centerline of the arteries and is defined in terms of an x,y coordinate plus a radius, which are output from the skeletonization filter. The point ordering CNN passes these data structures through layers of convolutional and pooling layers and outputs augmented data structures where the points are ordered based on their position along the length or a coronary tree.

At block 316, using the 2D+r ordered points clouds of the two frames, the modeling software 110 is configured to project the data points. For example, points of one view (one frame) are projected and matched to the projected points of the other view (second frame) between each pair of rays calculated. For example, modeling software 110 can use triangulation to determine the 3D reconstruction of the artery captured in the two still frames (which are 2D). Triangulation refers to the process of determining a point in 3D space given its projections onto two or more images. Triangulation is sometimes also referred to as reconstruction. The modeling software 110 is configured to capture the 3D ordered point cloud from the projection at block 318. The 3D ordered point cloud has x, y, z coordinates for each of the data points in the projection.

At block 320, the modeling software 110 is configured to perform point regression using the 3D ordered point cloud. Linear regression consists of finding the best-fitting straight line through the points. The best-fitting line is called a regression line. For each x, y, z point, the modeling software 110 associates its respective radius r (from blocks 310, 312, 314), such that a 3D structure of the reconstructed artery 170 is formed at block 322. In some implementations, a point regression CNN 118 can be used depicted in FIG. 1. The point regression CNN 118 is a neural network architecture that takes as input the sets of ordered 3D point clouds. The CNN then passes these two data structures through a series of convolutional and pooling layers and outputs a single 3D ordered point cloud defined in terms of the x,y,z coordinates, a radius, and a label identifying the particular branch.

Figure 4:
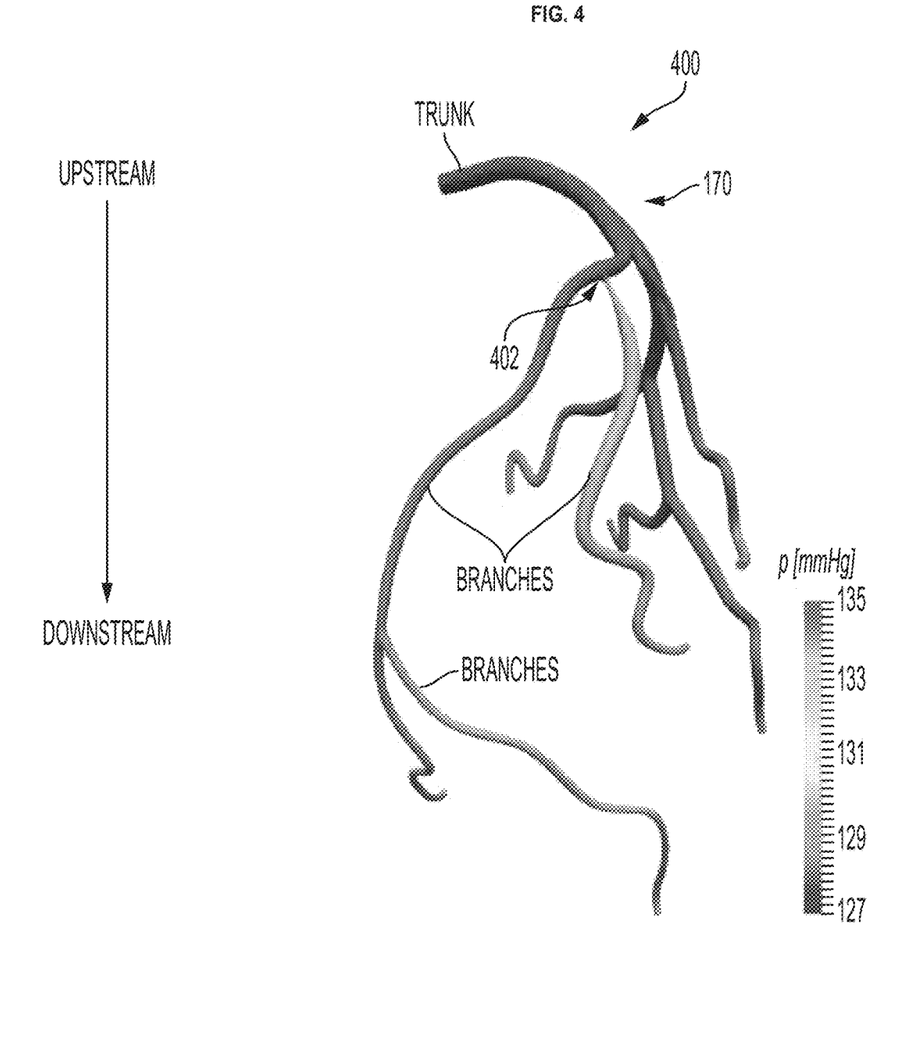
FIG. 4 depicts an example of the detailed blood pressure field that is produced by a fractional flow reserve simulation for a given patient-specific geometry according to embodiments of the invention.

FIG. 4 depicts a fractional flow reserve simulation 400 for a given patient-specific geometry according to embodiments of the invention. The simulation can be performed by simulation software 112 using the reconstructed coronary artery 170 (e.g., 3D model). The flow model 152 of simulation software 112 is configured to solve computation fluid dynamic equations given the reconstructed coronary artery 170. FIG. 4 identifies one location of narrowing/stenosis 402 in the reconstructed coronary artery 170.

Fractional flow reserve (FFR) is a technique used in coronary catheterization to measure pressure differences across a coronary artery stenosis (narrowing, usually due to atherosclerosis) to determine the likelihood that the stenosis impedes oxygen delivery to the heart muscle (myocardial ischemia). Fractional flow reserve is defined as the pressure after (distal to) a stenosis relative to the pressure before the stenosis. The result is an absolute number; an FFR of 0.80 means that a given stenosis causes a 20% drop in blood pressure. In other words, FFR expresses the maximal flow down a vessel in the presence of a stenosis compared to the maximal flow in the hypothetical absence of the stenosis. During coronary catheterization, a catheter is inserted into the femoral (groin) or radial arteries (wrist) using a sheath and guidewire. In the state-of-the-art, FFR uses a small sensor on the tip of the wire (commonly a transducer) to measure pressure, temperature and flow to determine the exact severity of the lesion. This is done during maximal blood flow (hyperemia), which can be induced by injecting products such as adenosine or papaverine. A pullback of the pressure wire is performed, and pressures are recorded across the vessel.

However, unlike the state-of-the-art, embodiments of the invention do not require a pressure sensor (transducer) added to the tip of the catheter to measure/determine pressure. Instead, the computational fluid dynamics simulation creates a representation of the in-vivo blood pressure field that can be probed at locations upstream and downstream of a stenosis to produce the same result as a pressure wire.

At this point, the 3D model 170 is input into a simulation pipeline along with the patient's systemic blood pressure, contrast injection information, and set of contrast positions. The set of contrast positions are a sequence of angiogram frames from the videos showing the flow of contrast (i.e., dye) through the artery of the patient 140 during imaging by the imaging system 136. A computational mesh of the reconstructed coronary artery (tree) 170 is generated (by the modeling software 110 and/or the simulation software 112) that includes the narrowing caused by the identified stenoses.

The simulation software 112 is configured to perform an initial blood flow simulation to tune the coronary arterial resistances used as boundary conditions in the simulation, based on the flow model 152 matching simulated contrast motion in the reconstructed coronary artery (tree) 170 to the observed contrast motion in the angiogram frames. At this point, a completely patient specific representation of the hemodynamics has been generated (as depicted in FIG. 4). FIG. 4 represents the simulation of pressure caused by the hemodynamics of blood flow with respect to time. Optionally, the hemodynamics of the simulation of pressure for the blood flow can be an average of pressure such as a time average of pressure taken across the reconstructed coronary artery (tree) 170 at respective locations, and/or the hemodynamics of the simulation of pressure for the blood flow can be taken when the heart has just relaxed, contracted, etc. (i.e., at a point in time (i.e., snapshot) selected relative to the heart cycle).

Figure 5A:
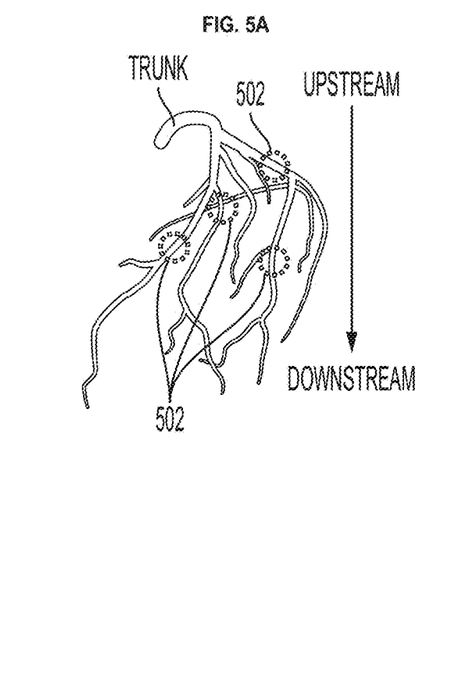
FIG. 5A depicts location of stenosis in the reconstructed coronary artery according to embodiments of the invention.

FIG. 5A depicts locations of stenosis in the reconstructed coronary artery 170 according to embodiments of the invention. FIG. 5A represents the original artery geometry, e.g., prior to making simulated corrections discussed in FIG. 5B. The simulation software 112 is configured to determine the location of stenosis by identifying areas where the pressure drops starting upstream and proceeding downstream, where the trunk is furthest upstream and proceeding toward the tips of each respective branch downstream. Given the computer model of a coronary tree with the variation in arterial diameter along each segment, the location of a stenosis is found by iterating over all arterial segments and identifying regions where the diameter changes abruptly, first reducing in diameter, then returning to the original diameter. The degree of stenosis can be determined based on the minimum and maximum diameters in this region. In this example, the four circles labeled 502 each represent a location of stenosis in the patient 140 identified in real-time as the patient 140 is undergoing the heart catheterization procedure. FIG. 5A represents a baseline simulation of the stenosis for the patient, and the simulation software 112 is configured to perform corrections to one or more stenoses.

Figure 5B:
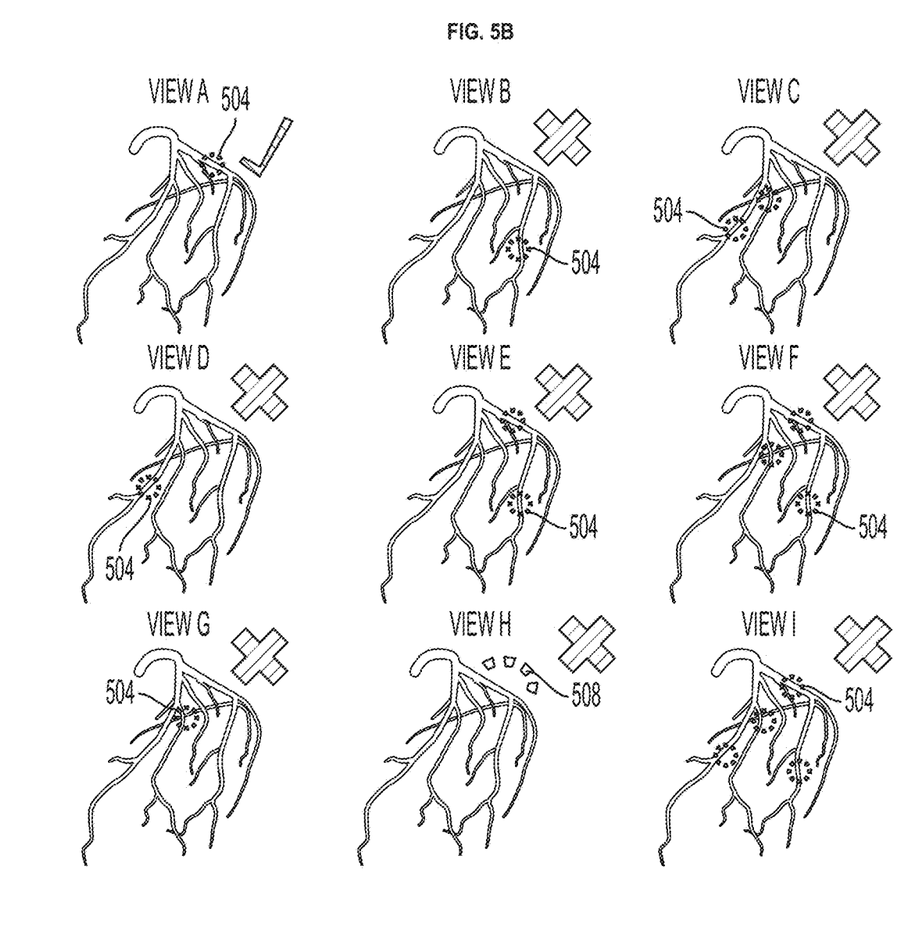
FIG. 5B depicts geometries representing alternate treatment plans for stenosis simulated according to embodiments of the invention.

FIG. 5B depicts geometries representing alternate treatment plans for stenosis simulated by simulation software 112 according to embodiments of the invention. FIG. 5B illustrates an array of simulations for the heart 134 of patient 140 in real-time as the patient is undergoing cardiac catheterization in the catheterization laboratory 130. The geometries represent alternate treatment plans in view A through view I in the example array. In view A through view I, the location of (corrective) stents within the simulated geometry are represented by circles 504 and the location of a coronary arterial bypass graft (CABG) 508 is represented by a dotted line in the example treatment plans.

An example scenario is provided below. Given a baseline simulation of the diseased state (defined in terms of one or more stenoses as depicted in FIG. 5A), a set of predictive simulations is performed by the simulation software 112 altering the geometrical model to simulate the effects of stent insertion by restoring the arterial diameter to its normal healthy state. For every identified stenosis, all permutations of potential stent insertion can be simulated to provide a quantitative measure of the restoration of normal healthy blood flow as shown in FIG. 5B. For severely diseased arteries, where CABG may be more applicable, simulations can be performed by generating arterial segments in the geometrical model to simulate the potential blood flow restoration. The blood flow improvement for each permutation depicted in FIG. 5B can be weighted against the potential risk associated with each procedure based on a database 122 of population statistics. An objective function L is configured to determine the optimal outcome by weighting the following factors: effect on blood flow (LF), pressure gradients (LP), and sheer stress (LS) throughout the geometrical model (i.e., the 3D model 170), the number of stents required (LN), and the risk related to a CABG or stent procedure (risk associated with performing coronary artery bypass graft surgery (RCABG) and risk associated with deploying multiple stents, (RMS) respectively). Additionally, the model can include a learned component (RL), which adaptively updates the parameters of the objective function based on outcomes. For example, by analyzing previous patient data, a relationship can be found between smoking and an increased risk of procedures requiring general anesthetic. This information could be included in the function below through use of the learned component RL: L=f(LF, LP, LS, LN, RC, RMS, RL).

The option in view A through view I that minimizes this objective function L is considered to be the optimal treatment plan for the reconstructed coronary artery 170 (FIG. 4). This plan (e.g., in view A) is then suggested to the clinician, and the clinician follows the treatment plan including the placement of stents and/or bypass graft to correct the stenosis of the heart 134 all while heart catheterization of the patient 140 is occurring. For example, the computer system 110 is configured to send the best determined treatment plan (e.g., view A) and/or the best group of treatment plans to the user device 142 at the catheterization laboratory 130. If it is requested by the clinician (via user devices 142), multiple options can be suggested, and further information provided about why the scenario was not the optimum. This information would be acquired by interrogating the resultant objecting function to ascertain which of the factors most contributed to it. Such feedback would help to increase the clinician's confidence in the technology.

Furthermore, once the chosen treatment plan has been undertaken, the anatomical and functional model could be updated with post-operation scans. Such an update would allow the clinician to anticipate adverse outcomes, such as restenosis due to sub-optimal stent placement, and act on them prior to their occurrence. Additionally, the anatomical and functional model that is produced through this process may be kept in the patient's records, in order to simulate the effects of future occurrences. For example, in the scenario of multiple stent insertions, simulations can be performed in order to determine the detrimental effects of restenosis in one or more of the deployed stents to produce a risk assessment and provide information to the clinician as to which patients require more frequent follow up consultation.

Figure 6:
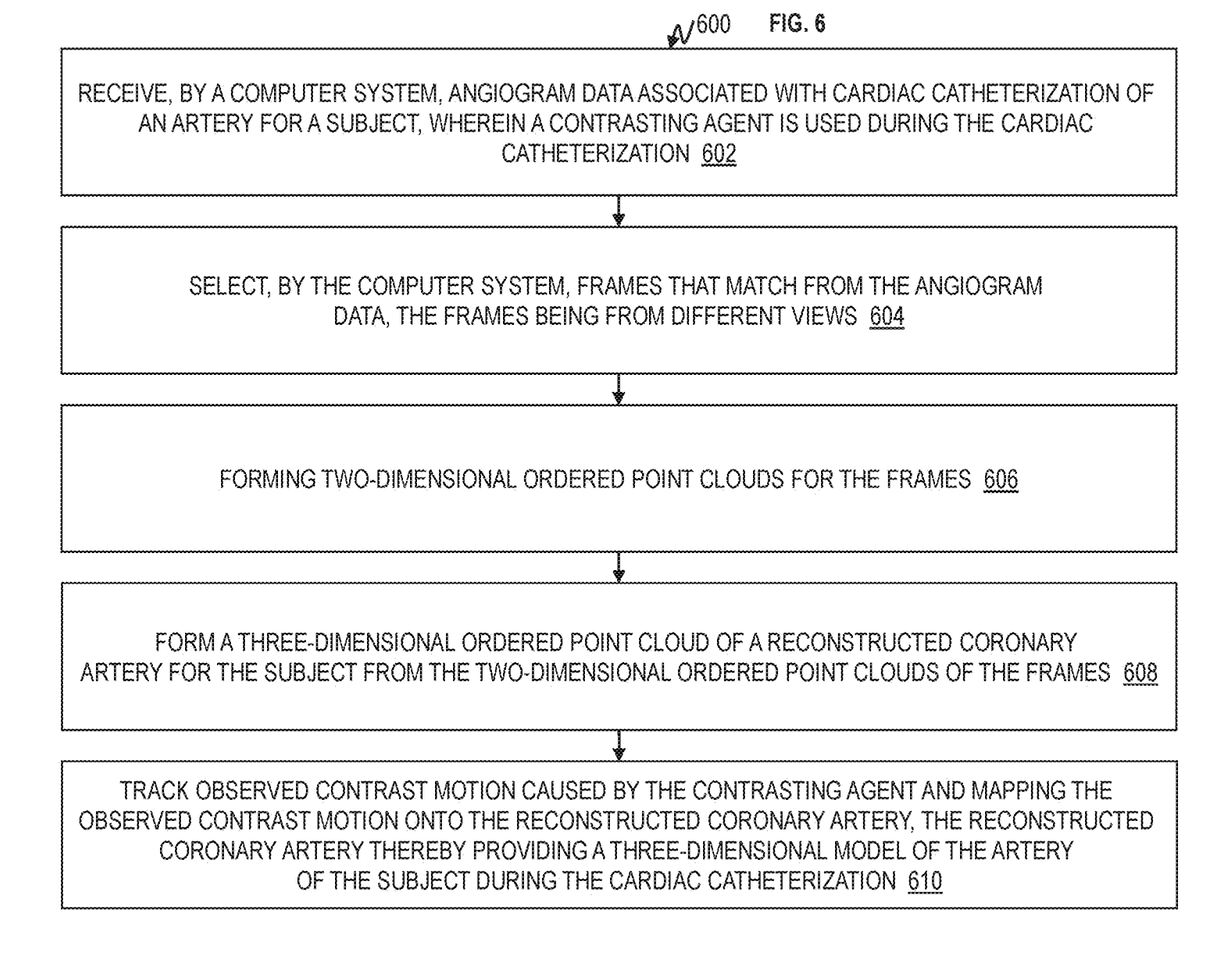
FIG. 6 depicts a flowchart of a computer-implemented method for coronary intervention according to embodiments of the invention.

FIG. 6 depicts a flowchart 600 of a computer-implemented method for coronary reconstruction and/or intervention according to embodiments of the invention. At block 602, the computer system 100 is configured to receive angiogram data associated with cardiac catheterization of an artery for a subject 140, where a contrasting agent is used during the cardiac catheterization (depicted in FIG. 1). At block 604, the computer system 100 is configured to select frames (at block 206 and/or 302) that match (i.e., have a matching point) from the angiogram data, the frames being from different views. At block 606, the computer system 100 is configured to form two-dimensional ordered point clouds (at block 314) for the frames. At block 608, the computer system 100 is configured to form a three-dimensional ordered point cloud (at block 318) of a reconstructed coronary artery 170 (at block 206 and 322) for the subject 140 from the two-dimensional ordered point clouds of the frames. At block 610, the computer system 100 is configured to track observed contrast motion (at block 208) caused by the contrasting agent and mapping the observed contrast motion onto the reconstructed coronary artery, the reconstructed coronary artery thereby providing a digital three-dimensional model (view) of the artery of the subject during the cardiac catheterization. The observed contrast motion is the movement of the dye through the artery. At a point, the flow dye is constricted/narrowed and this can be indicative of stenosis when the flow is wider upstream and downstream from the constricted/narrowed point.

Forming the two-dimensional ordered point clouds for the frames comprises segmenting (at blocks 306, 308, 310), by the computer system 100, the frames into an arterial structure, thereby separating out a background part and a catheter part (at block 306 and 308). Forming the two-dimensional ordered point clouds for the frames further comprises: skeletonizing, by the computer system 100, the arterial structure in the frames into centerline points, the centerlines points being associated with a radius (at block 308 and 310) and ordering, by the computer system 100, the centerline points to generate the two-dimensional ordered point clouds for the frames. Forming the three-dimensional ordered point cloud from the two-dimensional ordered point clouds of the frames comprises projecting points of the two-dimensional ordered point clouds for the frames of the different views to create the three-dimensional ordered point cloud (at block 316).

The computer system 100 is configured to perform a simulation using the reconstructed coronary artery 170, and tuning coronary arterial resistances in the simulations by matching simulated contrast motion to the observed contrast motion (at block 208) in the angiogram data associated with the cardiac catheterization for the subject, thereby generating the hemodynamics of the reconstructed coronary artery 170 (at FIG. 4) for the subject 140 along with identifying stenosis (e.g., stenoses 402 and 502) in the reconstructed coronary artery 170.

The reconstructed coronary artery 170 comprises one or more locations of stenosis 402, 502), and further comprising for the reconstructed coronary artery, performing a simulation of alternate treatment plans designed to correct the one or more locations of stenosis (depicted in views A-I in FIG. 5B). Where performing the simulation of the alternate treatment plans (e.g. views A-I) to correct the one or more locations of stenosis displays alternate treatments for the one or more locations of stenosis, the alternate treatments comprise one or more stents (stents 504) and one or more arterial bypass grafts (508).

Technical benefits and advantages of embodiments of the invention include novel methods to suggest an optimal, patient-specific treatment plan that will minimize negative outcomes but taking all possible treatment plans into account. The method allows for multiple scenarios to be simulated during an intervention (heart catheterization) in real-time. Embodiments of the invention include factors such as sheer stress in the simulation and objective function, which allow for an understanding of the future impact of any intervention. The 3D model and simulations are able to be reused in future patient visits to assess the effect of different activities and lifestyle changes on the patient's coronary blood flow and provide the ability to update the objective function based on previous patient outcomes and population statistics, through a learned process. Technical benefits and advantages include by using angiographic data (rather than only CT) the embodiments of the invention produce more accurate results than previous methods by incorporating patient specific functional information. The system improves patient outcomes by reducing the number of sub-optimal treatment decisions. This is turn reduce the cost of interventions and after-care. Simulating the outcome of different treatments produces results that would otherwise not be considered by the clinician. Additionally, the system requires only a small number of angiographic scans to produce a full functional and anatomical model of the coronary arteries, thereby reducing the amount of radiopaque dye that is used (because this can be harmful in large doses) and the amount of time both the clinician and patient are exposed to harmful x-ray radiation. The system allows the clinician to view the optimal treatment outcome, as well as multiple other outcomes if more information is required by clinician in addition to the particular outcome that was chosen.

Figure 7:
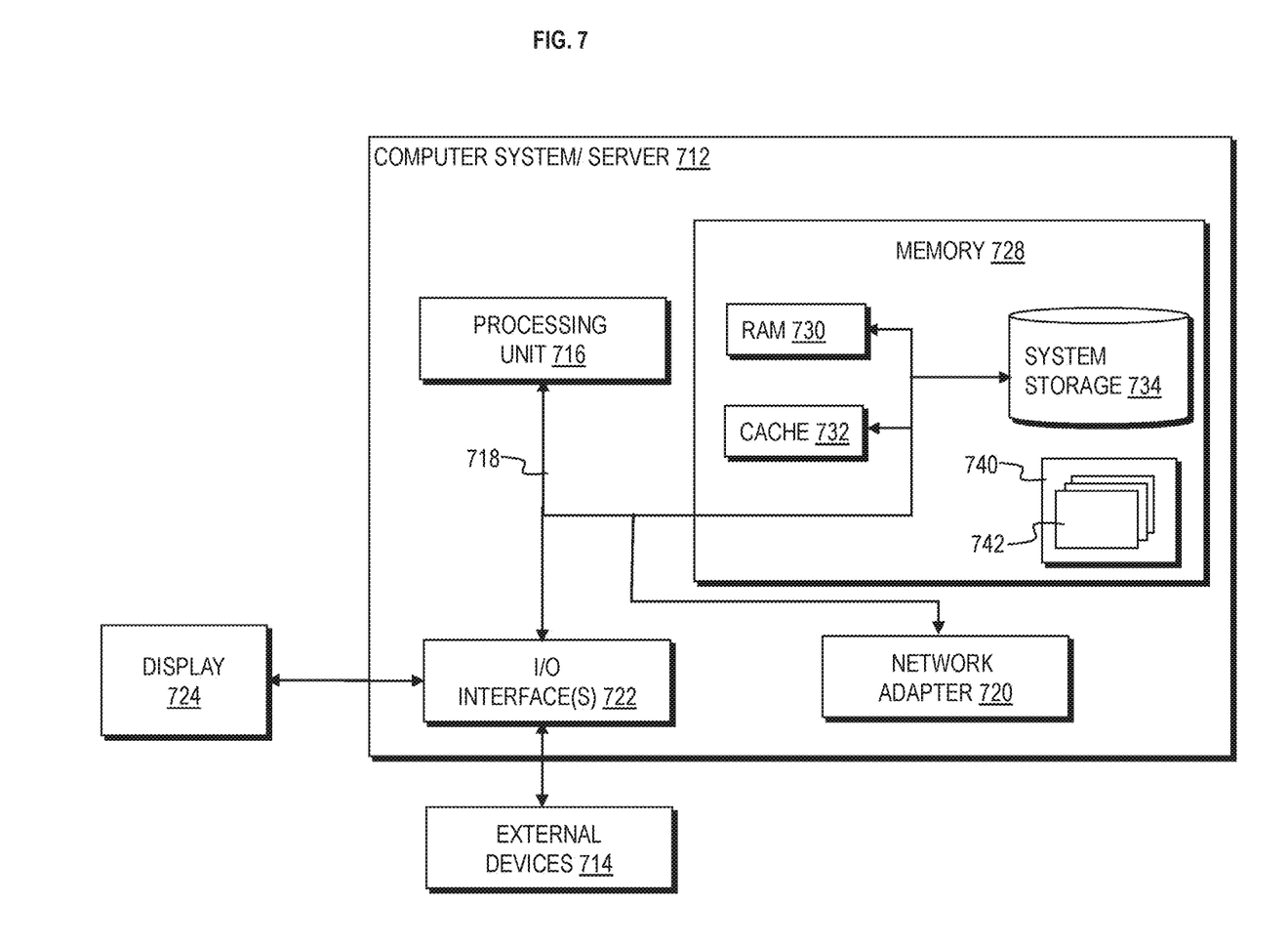
FIG. 7 depicts a schematic of an example computing system having elements and functions which operate as discussed herein in FIGS. 1-6 according to embodiments of the invention.

FIG. 7 depicts a schematic of an example computing system 712 according to embodiments of the present invention. The computer system/server 712 can be operational with numerous other general purpose or special purpose computing system environments or configurations. The computer system/server 712 can be representative of various types of computer systems in system 150. The functions and capabilities of computing system 712 can be utilized in FIGS. 1-6 to implement one or more features of elements 100, 136, 138, 142, 144, 180 according to embodiments of the invention.

Examples of well-known computing systems, environments, and/or configurations that can be representative of and/or include elements of computer system/server 712 include, but are not limited to, personal computer systems, phones (e.g., cellphones, smart phones, etc.), server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 712 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 712 may be practiced in distributed cloud computing environments where tasks are performed by remote processing devices that are linked through a communications network. In a distributed cloud computing environment, program modules may be located in both local and remote computer system storage media including memory storage devices.

The components of computer system/server 712 may include, but are not limited to, one or more processors or processing units 716, a system memory 728, and a bus 718 that couples various system components including system memory 728 to processor 716. Bus 718 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 712 typically includes a variety of computer system readable media. Such media may be any available media that is accessible by computer system/server 712, and it includes both volatile and non-volatile media, removable and non-removable media. The system memory 728 can include computer system readable media in the form of volatile memory, such as random access memory (RAM) 730 and/or cache memory 732. Computer system/server 712 may further include other removable/non-removable, volatile/non-volatile computer system storage media. By way of example only, storage system 734 can be provided for reading from and writing to a nonremovable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 718 by one or more data media interfaces. Memory 728 may include at least one program product having a set (e.g., at least one) of program modules that are configured to carry out the functions of embodiments of the invention.

Program/utility 740, having a set (at least one) of program modules 742, may be stored in memory 728 by way of example, and not limitation, as well as an operating system, one or more application programs, other program modules, and program data. Each of the operating system, one or more application programs, other program modules, and program data or some combination thereof, may include an implementation of a networking environment. Program modules 742 generally carry out the functions and/or methodologies of embodiments of the invention as described herein.

Computer system/server 712 may also communicate with one or more external devices 714 such as a keyboard, a pointing device, a display 724, etc.; one or more devices that enable a user to interact with computer system/server 712; and/or any devices (e.g., network card, modem, etc.) that enable computer system/server 712 to communicate with one or more other computing devices. Such communication can occur via Input/Output (I/O) interfaces 722. Still yet, computer system/server 712 can communicate with one or more networks such as a local area network (LAN), a general wide area network (WAN), and/or a public network (e.g., the Internet) via network adapter 720. As depicted, network adapter 720 communicates with the other components of computer system/server 712 via bus 718. It should be understood that although not shown, other hardware and/or software components could be used in conjunction with computer system/server 712. Examples, include but are not limited to: microcode, device drivers, redundant processing units, external disk drive arrays, RAID systems, tape drives, and data archival storage systems, etc.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a wave-guide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate possible implementations of fabrication and/or operation methods according to various embodiments of the present invention. Various functions/operations of the method are represented in the flow diagram by blocks. In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method for generating display of a coronary reconstruction, the computer-implemented method comprising: receiving, by a computer system, angiogram data during cardiac catheterization of an artery for a subject, wherein a contrasting agent is used during the cardiac catheterization; selecting, by the computer system, frames that match from the angiogram data according to a same cycle of a heart for an electrocardiogram trace, the frames being from different views; forming two-dimensional ordered point clouds for the frames; forming a three-dimensional ordered point cloud of a reconstructed coronary artery for the subject from the two-dimensional ordered point clouds of the frames; generating, for graphical display by the computer system, a three-dimensional model of the reconstructed coronary artery of the subject during the cardiac catheterization by mapping observed contrast motion caused by the contrasting agent onto the reconstructed coronary artery; and performing, by the computer system, a simulation of hemodynamics for the reconstructed coronary artery during the cardiac catheterization; and rating multiple outcomes of the simulation based at least in part on heart catheterization data while the subject is undergoing the cardiac catheterization.

2. The computer-implemented method of claim 1, wherein forming the two-dimensional ordered point clouds for the frames comprises segmenting, by the computer system, the frames into an arterial structure, thereby separating out a background part and a catheter part; and
    wherein the simulation generates a representation of an in-vivo blood pressure field that can be probed at locations upstream and downstream of a stenosis, thereby allowing the catheter part to be free of a pressure sensor.

3. The computer-implemented method of claim 1, wherein forming the two-dimensional ordered point clouds for the frames further comprises:
    skeletonizing, by the computer system, an arterial structure in the frames into centerline points, the centerline points being associated with a radius; and
    ordering, by the computer system, the centerline points to generate the two-dimensional ordered point clouds for the frames.

4. The computer-implemented method of claim 1, wherein forming the three-dimensional ordered point cloud from the two-dimensional ordered point clouds of the frames comprises projecting points of the two-dimensional ordered point clouds for the frames of the different views to create the three-dimensional ordered point cloud.

5. The computer-implemented method of claim 1 further comprising tuning coronary arterial resistances in the simulation by matching simulated contrast motion to the observed contrast motion in the angiogram data associated with the cardiac catheterization for the subject, thereby generating the hemodynamics of the reconstructed coronary artery for the subject along with identifying stenosis in the reconstructed coronary artery.

6. The computer-implemented method of claim 1, wherein:
    the reconstructed coronary artery comprises one or more locations of stenosis; and
    the computer-implemented further comprises, for the reconstructed coronary artery, performing a simulation of alternate treatment plans designed to correct the one or more locations of stenosis.

7. The computer-implemented method of claim 6, wherein performing the simulation of the alternate treatment plans to correct the one or more locations of stenosis displays alternate treatments for the one or more locations of stenosis, the alternate treatments comprise one or more stents and one or more arterial bypass grafts.

8. A system for generating display of a coronary reconstruction, the system comprising: a processor; and memory communicatively coupled to the processor and comprising computer-executable instructions that, when executed by the processor, cause the processor to perform a method comprising: receiving, by the processor, angiogram data during cardiac catheterization of an artery for a subject, wherein a contrasting agent is used during the cardiac catheterization; selecting, by the processor, frames that match from the angiogram data according to a same cycle of a heart for an electrocardiogram trace, the frames being from different views; forming two-dimensional ordered point clouds for the frames; forming a three-dimensional ordered point cloud of a reconstructed coronary artery for the subject from the two-dimensional ordered point clouds of the frames; generating, for graphical display by the processor, a three-dimensional model of the reconstructed coronary artery of the subject during the cardiac catheterization by mapping observed contrast motion caused by the contrasting agent onto the reconstructed coronary artery; and performing, by the processor, a simulation of hemodynamics for the reconstructed coronary artery during the cardiac catheterization; and rating multiple outcomes of the simulation based at least in part on heart catheterization data while the subject is undergoing the cardiac catheterization.

9. The system of claim 8, wherein forming the two-dimensional ordered point clouds for the frames comprises segmenting, by the processor, the frames into an arterial structure, thereby separating out a background part and a catheter part; and
    wherein the simulation generates a representation of an in-vivo blood pressure field that can be probed at locations upstream and downstream of a stenosis, thereby allowing the catheter part to be free of pressure sensor.

10. The system of claim 8, wherein forming the two-dimensional ordered point clouds for the frames further comprises:
    skeletonizing, by the computer system, an arterial structure in the frames into centerline points, the centerline points being associated with a radius; and
    ordering, by the computer system, the centerline points to generate the two-dimensional ordered point clouds for the frames.

11. The system of claim 8, wherein forming the three-dimensional ordered point cloud from the two-dimensional ordered point clouds of the frames comprises projecting points of the two-dimensional ordered point clouds for the frames of the different views to create the three-dimensional ordered point cloud.

12. The system of claim 8, further comprising tuning coronary arterial resistances in the simulation by matching simulated contrast motion to the observed contrast motion in the angiogram data associated with the cardiac catheterization for the subject, thereby generating the hemodynamics of the reconstructed coronary artery for the subject along with identifying stenosis in the reconstructed coronary artery.

13. The system of claim 8, wherein:
    the reconstructed coronary artery comprises one or more locations of stenosis; and
    the system is further configured to, for the reconstructed coronary artery, perform a simulation of alternate treatment plans designed to correct the one or more locations of stenosis.

14. The system of claim 13, wherein performing the simulation of the alternate treatment plans to correct the one or more locations of stenosis displays alternate treatments for the one or more locations of stenosis, the alternate treatments comprising one or more stents and one or more arterial bypass grafts.

15. A computer program product for generating display of a coronary reconstruction, the computer program product comprising a computer readable storage medium having program instructions embodied therewith, wherein the computer readable storage medium is not a transitory signal per se, the program instructions executable by a computer system to cause the computer system to perform a method comprising: receiving, by the computer system, angiogram data during cardiac catheterization of an artery for a subject, wherein a contrasting agent is used during the cardiac catheterization; selecting, by the computer system, frames that match from the angiogram data according to a same cycle of a heart for an electrocardiogram trace, the frames being from different views; forming two-dimensional ordered point clouds for the frames; forming a three-dimensional ordered point cloud of a reconstructed coronary artery for the subject from the two-dimensional ordered point clouds of the frames; and generating, for graphical display by the computer system, a three-dimensional model of the reconstructed coronary artery of the subject during the cardiac catheterization by mapping observed contrast motion caused by the contrasting agent onto the reconstructed coronary artery; and performing, by the computer system, a simulation of hemodynamics for the reconstructed coronary artery during the cardiac catheterization; and rating multiple outcomes of the simulation based at least in part on heart catheterization data while the subject is undergoing the cardiac catheterization.

16. The computer program product of claim 15, wherein forming the two-dimensional ordered point clouds for the frames comprises segmenting, by the computer system, the frames into an arterial structure, thereby separating out a background part and a catheter part; and
wherein the simulation generates a representation of an in-vivo blood pressure field that can be probed at locations upstream and downstream of a stenosis, thereby allowing the catheter part to be free of pressure sensor.

17. The computer program product of claim 15 further comprising tuning coronary arterial resistances in the simulation by matching simulated contrast motion to the observed contrast motion in the angiogram data associated with the cardiac catheterization for the subject, thereby generating the hemodynamics of the reconstructed coronary artery for the subject along with identifying stenosis in the reconstructed coronary artery.

18. The computer program product of claim 15, wherein:
the reconstructed coronary artery comprises one or more locations of stenosis; and
the method performed by the computer system further comprises, for the reconstructed coronary artery, performing a simulation of alternate treatment plans designed to correct the one or more locations of stenosis.

19. The computer-implemented method of claim 1, wherein the rating of the multiple outcomes of the simulation is based at least in part on a number of stents required.

* * * * *